United States Patent
Hugo et al.

[11] Patent Number: 6,062,858
[45] Date of Patent: May 16, 2000

[54] MEDICAL OR DENTAL HANDPIECE WITH A TOOL FOR PROCESSING BY MACHINING

[75] Inventors: Burkhard Hugo, Hettstadt; Walter Mössle, Mittelbiberach, both of Germany

[73] Assignee: Kaltenbach & Voigt GmbH, Biberach, Germany

[21] Appl. No.: 09/129,083

[22] Filed: Aug. 5, 1998

[30] Foreign Application Priority Data

Aug. 20, 1997 [DE] Germany .............. 197 36 240

[51] Int. Cl.[7] .............. A61C 1/07; A61C 3/03; A61C 3/08
[52] U.S. Cl. .............. 433/119; 433/125; 433/118
[58] Field of Search .............. 433/118, 119, 433/125, 126, 165, 166

[56] References Cited

U.S. PATENT DOCUMENTS

| | | | |
|---|---|---|---|
| 2,141,304 | 12/1938 | Kirwan et al. | 433/118 X |
| 3,401,690 | 9/1968 | Martin | 433/119 X |
| 3,978,852 | 9/1976 | Annoni | 433/118 X |
| 4,353,696 | 10/1982 | Bridges | 433/125 |
| 5,010,906 | 4/1991 | Preciutti | 132/323 |
| 5,423,102 | 6/1995 | Madison | 15/22 |

FOREIGN PATENT DOCUMENTS

| | | |
|---|---|---|
| 4211625 A1 | 10/1993 | Germany . |
| 2074077 | 10/1981 | United Kingdom . |
| WO96/1402 | 5/1996 | WIPO . |

*Primary Examiner*—Nicholas D. Lucchesi
*Attorney, Agent, or Firm*—Fitzpatrick, Cella, Harper & Scinto

[57] ABSTRACT

In the case of a medical or dental handpiece with a tool for the processing of body tissue or of a substitute material by machining, wherein the tool comprises an, in particular, elongated processing section extending from a base part connected to the handpiece by a detachable connecting device, the processing section having at least one abrasive working face extending in its longitudinal direction and/or transverse thereto, the handpiece has an oscillating drive for the tool, in particular for a frequency in the ultrasonic range, an articulation is assigned to the connecting device, and the axis of the articulation extends approximately in the longitudinal direction of the longitudinal axis of the processing section, approximately at a right angle thereto or in an angular range lying in between.

19 Claims, 3 Drawing Sheets

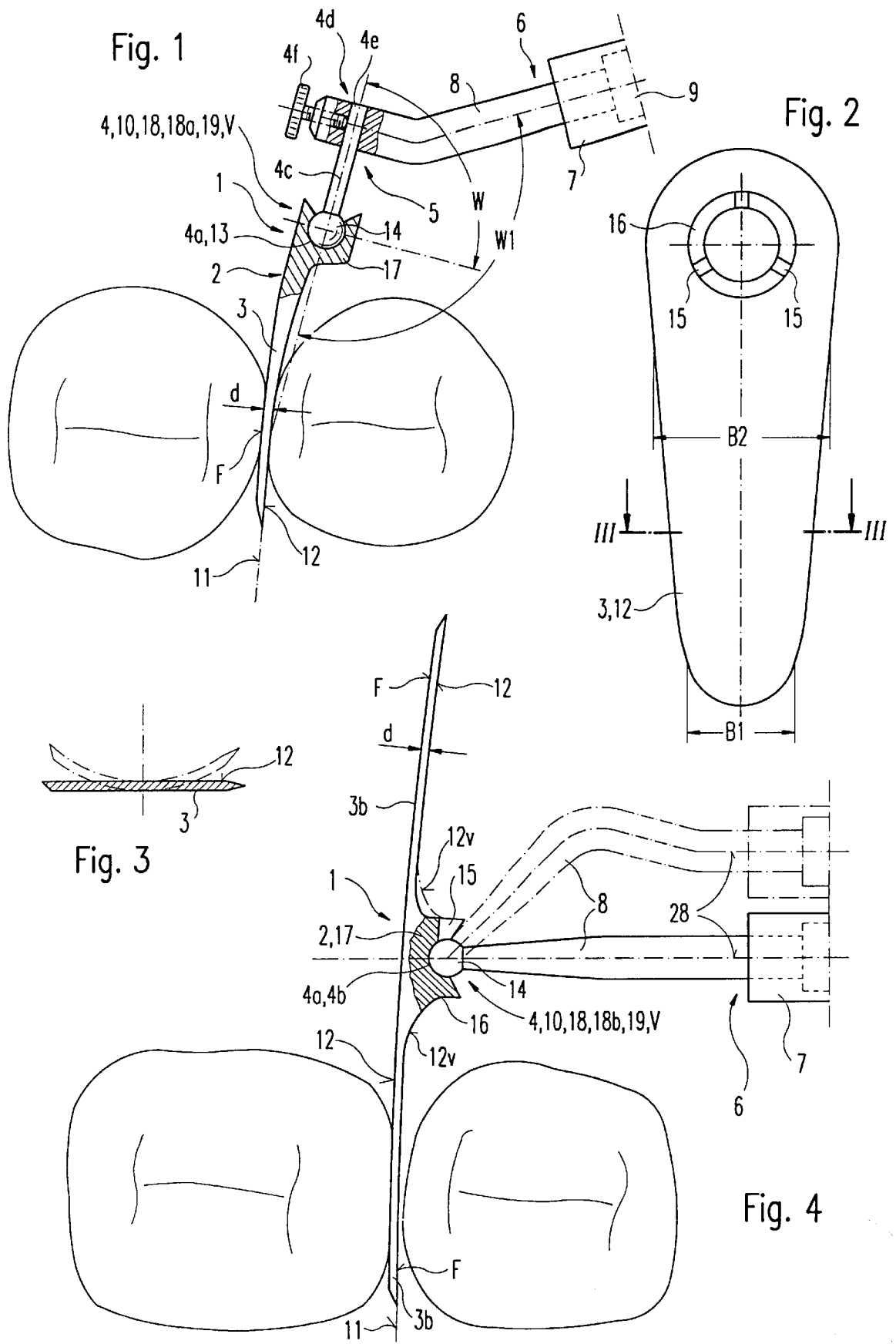

MEDICAL OR DENTAL HANDPIECE WITH A TOOL FOR PROCESSING BY MACHINING

BACKGROUND OF THE INVENTION

1. Technical Field

The invention relates to a medical or dental handpiece with a tool for the processing of body tissue or of a substitute material by machining.

2. Background Information

In WO 96/14024 a tool is described having an abrasive processing section which is effective laterally and frontally and which is suitable, with an oscillating drive in the sense of a vibration which is transmitted to the tool by a dental handpiece, for preparing a lateral cavity in a tooth. The magnitude of the amplitudes of the oscillating movements is relatively small in the sense of a vibration, with the frequency preferably lying in the ultrasonic range. With this known design the processing section is a processing head which is thickened with respect to the tool shank and which has a cross-sectional shape converging towards its free end. On the side located opposite the lateral processing section the tool has a smooth face. By this means the known tool is suitable for working a cavity in the approximal region of a tooth. In the course of this working procedure the processing section is preferably lowered from the occlusal region towards the cervical region. In this connection the cavity may have already been worked beforehand by means of a rotary tool or it may also be prepared with the processing section without preliminary work. In this connection the adjacent tooth remains unimpaired, since the smooth face located opposite the processing section does not damage the adjacent tooth. The abrasiveness of the effective working faces of the processing section is created by means of a studding of juxtaposed small grains of hard material, preferably of diamond. In functional operation the small hard grains prove to be a plurality of cutting edges, the working faces that are present in each case being effective over substantially their entire area.

The tool according to WO 96/14024 has working faces directed transverse to one another—for example, at least one working face extending in its longitudinal direction and one front face extending transverse thereto—and by reason of a drive having three-dimensional amplitudes it is adapted not only to process surfaces, as is conventional in the case of files, but also to work holes or cavities, in particular blind holes.

The amplitudes of the oscillating movements of the processing section in functional operation may be executed by three-dimensional, circular or elliptical movements in the sense of a vibration. In order to avoid jamming in the course of extracting the tool from the cavity, the processing section has a cross-sectional shape that is convergent towards its free end.

In addition, files for the surface treatment of teeth by machining have become known that have an abrasive working face on a lateral face of a file blade extending along a tool shank. These known files are adapted for an oscillating movement of considerable amplitude length, for example several millimetres, the movement being directed in the longitudinal direction of the shank. These known files are not suitable to prepare a cavity on a tooth, specifically they are not suitable in particular for such a cavity that takes the form of a blind hole. This is predetermined by the fact that the known file does not have a working face extending transverse to the longitudinal direction of the shank and in addition an associated drive device is not adapted for drive movements directed transverse to the longitudinal direction of the shank. These known files are mainly used for the processing of surplus materials by machining and for processing of the surface, specifically also in the approximal tooth region, for which purpose they are suitable by virtue of their design comprising a thin file blade.

In practice, operations to process body tissue or corresponding substitute materials are necessary in various working positions of the tool in confined spatial conditions, as is the case for example in the oral cavity of a patient. For this reason special requirements exist with regard to being able to position the tool in different positions.

To this end it has already been proposed to integrate an adjusting device within a handpiece for holding a tool so that the tool with its holder is capable of being adjusted and positioned in different rotary positions with respect to the handpiece. However, in many cases this adjustability is not sufficient to obtain a favourable working position for the tool. In addition it is difficult and costly to integrate such an adjusting device into the handpiece, since for the purpose of avoiding visual impairments in the course of handling the handpiece the space available in the end region of the handpiece is limited.

SUMMARY OF THE INVENTION

The object underlying the invention is to improve the positioning capacity of the tool in the case of a handpiece of the existing type.

This object is achieved by a medical or dental handpiece with a tool for the processing of body tissue or of a substitute material by machining, wherein the handpiece comprises a casing and a handpiece shank supported therein which by means of an oscillating drive arranged in the casing is capable of being caused to vibrate, in particular at a frequency in the sonic or ultrasonic range, wherein the tool comprises an, in particular, elongated processing section extending from a base part connected to the handpiece by means of a detachable connecting device, and wherein the processing section has at least one abrasive working face extending in its longitudinal direction and/or transverse thereto, wherein the handpiece shank protrudes from the casing and an articulation is assigned to the connecting device, the axis of which articulation extends approximately in the longitudinal direction of the longitudinal axis of the processing section or approximately at a right angle thereto or in the angular range lying in between.

With this design according to the invention, outside the processing section or the holder of the tool the tool comprises an articulation that enables an adjustment of the processing section with respect to an axis of articulation extending along or transverse to its longitudinal axis. In this connection at least one working face of the processing section may extend along or transverse to the axis of articulation. By reason of this adjustability the range of application of the tool can be significantly extended, whereby the ease of handling is improved and points on the object to be processed that are difficult to access can be reached, in the case for example of a dental tool in the approximal tooth region and/or in the cervical region, in particular in the course of preparatory procedures in the region of the gingival margin.

In many cases it is advantageous, on the one hand on account of particular positions of the treatment site to be processed and/or on account of particular shapes of the treatment site, to carry out the abrasive processing operations in question with tools that differ with respect to their shape and size. In such cases a suitable tool should be connected in each instance to the holder for the tool after previous removal of another tool.

Therefore the object further underlying the invention is to design an existing handpiece in such a way that it is capable of being connected to the tool in simple manner.

This object is achieved by a medical or dental handpiece with a tool for the processing of body tissue or of a substitute material by machining, wherein the handpiece comprises a casing and a handpiece shank supported therein which by means of an oscillating drive arranged in the casing is capable of being caused to vibrate, in particular at a frequency in the sonic or ultrasonic range, wherein the tool comprises an, in particular, elongated processing section extending from a base part connected to the handpiece by means of a detachable connecting device, and wherein the processing section has at least one abrasive working face extending in its longitudinal direction and/or transverse thereto, wherein the connecting device is constituted by an interlocking device which is capable of being pushed over manually.

With this design according to the invention the tool can be connected to and detached from the holder of a handpiece in easy-to-handle manner and quickly, whereby secure retention of the tool can be achieved both with larger amplitudes, as is the case with conventional files that are moved back and forth, and with small amplitudes at a high frequency, preferably in the sonic or ultrasonic range, as is the case with brief oscillations in the sense of a vibration.

The object further underlying the invention is to design an existing tool in such a way that it has a greater working capacity or the site of processing can be processed with reduced handling effort.

This object is achieved by a medical or dental tool for a handpiece for the processing of body tissue or of a substitute material by machining, wherein the handpiece comprises a casing and a handpiece shank supported therein which by means of an oscillating drive arranged in the casing is capable of being caused to vibrate, in particular at a frequency in the sonic or ultrasonic range, wherein the tool comprises an, in particular, elongated processing section extending from a base part connected to the handpiece by means of a detachable connecting device, wherein the processing section has at least one abrasive working face extending in its longitudinal direction and/or transverse thereto, and wherein an articulation is assigned to the connecting device, wherein several processing sections are provided distributed about the axis of articulation.

With this design according to the invention the tool comprises several processing sections which may be of similar or different construction, for example with respect to their shape and/or size. By this means not only more tool substance is available, as a result of which the service life of the tool is extended, but processing sections that are suitable for different shapes and/or sizes of the site of processing can be brought into the working position, as a result of which the handling is significantly simplified and efficiency is significantly increased.

With all the designs according to the invention it should be taken into account in addition that the quality of the work can be improved, since by reason of the simplified handling the attention of the person performing the treatment can be directed more intently towards the treatment and the processing can be carried out with ergonomically easier movements.

The subclaims contain features that result in simple, small, functionally reliable structural designs which can be manufactured in cost-effective manner, that further simplify handling and further improve productive capacity, and that are suitable for special processing operations, in particular in the approximal and cervical tooth regions.

The invention and further advantages that can be achieved with it are elucidated in more detail below on the basis of advantageous designs and drawings. Illustrated are:

BRIEF DESCRIPTION OF THE DRAWINGS

FIG. 1 a tool according to the invention with a handpiece in its working position in the approximal region of a row of teeth in top view;

FIG. 2 the tool according to FIG. 1 in the side view from the right in a modified design and on an enlarged scale;

FIG. 3 the section III—III in FIG. 2;

FIG. 4 a tool according to the invention with a handpiece according to FIG. 1 in a modified design;

DESCRIPTION OF THE PREFERRED EMBODIMENT

Figure 5:
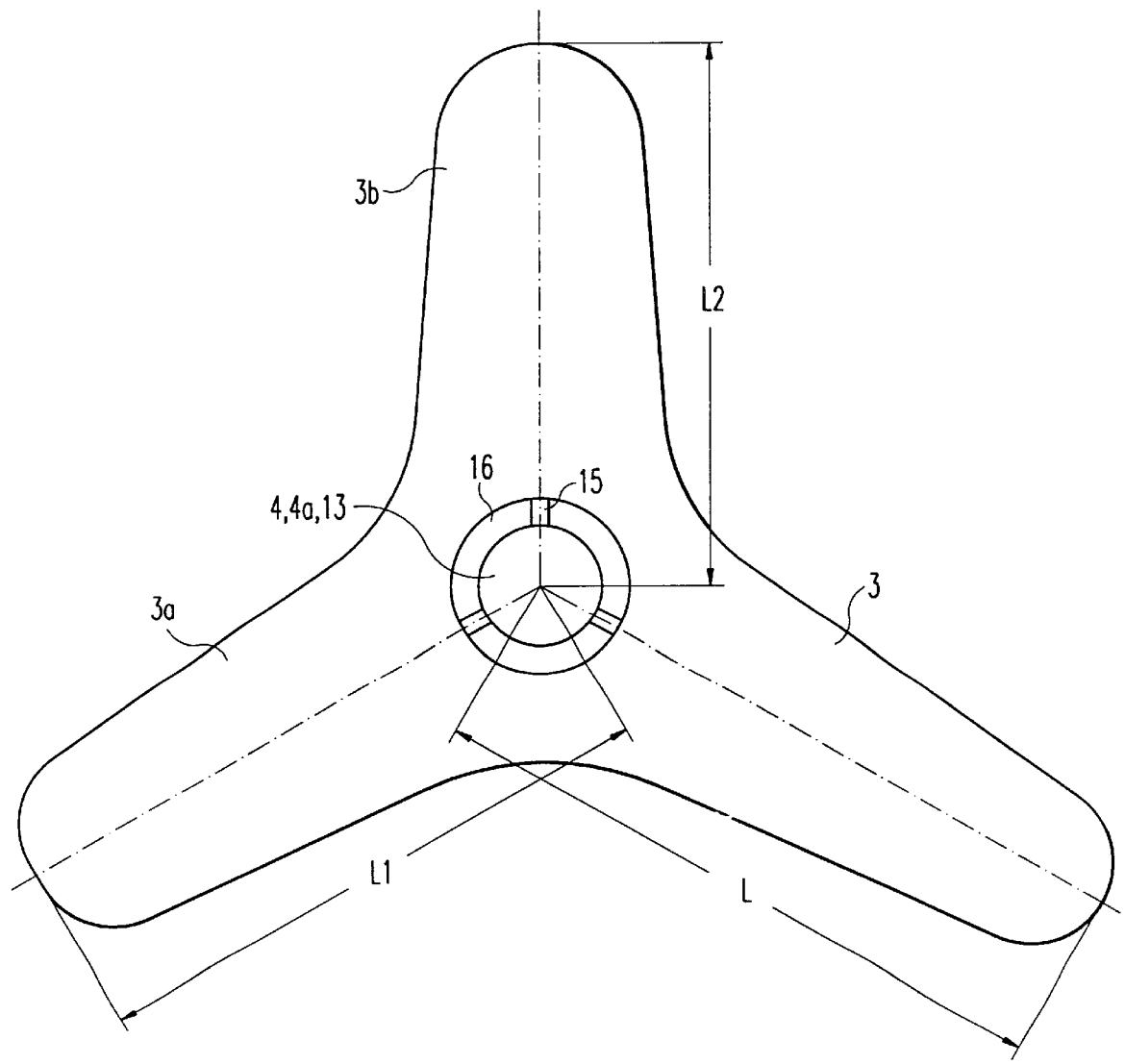
FIG. 5 the tool according to FIG. 4 in the side view from the right.

The tool which is designated generally by 1 comprises a tool shank or a base part 2 which is connected to a processing section 3 and constructed with an additional connecting part 4a which is part of a connecting device 4 and capable of being connected by means of the latter to a corresponding connecting part 4b of a holder 5 of a handpiece 6 which serves for retention and guidance of the elongated tool 1 in the course of processing. As regards the handpiece 6, merely the front part of a casing 7 is represented in which a handpiece shank 8 constituting the holder 5 is supported which protrudes from the casing 7 and which by means of a vibration generator 9 arranged in the casing 7 is capable of being caused to execute oscillating vibrations, the amplitudes of which may be directed, for instance, along the longitudinal axis 11 of the base part 2. But they may also point in different directions and be directed two-dimensionally, to be more exact in the form of a circle, or three-dimensionally.

The processing section 3 is an elongated and flat component in the form of a sword which has, on one broad side or on both broad sides, an abrasive working face 12 which is formed in a manner known as such by being studded with a plurality of preferably juxtaposed small hard grains of hard material, preferably of diamond, and which, for example, may be faced with diamonds in grainy manner. The abrasive layer should preferably merge in stepless manner with the adjacent regions of the working face. It is therefore advantageous to arrange or apply the abrasive covering in a depression or recess in suitably flush manner.

With a direction of view towards the broad side of the working face 12 or of the processing section 3, the free end of said processing section is rounded. With a direction of view towards the narrow side the processing section 3 may be straight or curved, whereby the working face 12 may be arranged on the concave side or on the convex side or on both sides.

The connecting device 4 is a quick-closing device, in particular a snap-action or interlocking device V, which is capable of being pressed together and also detached again by a certain expenditure of force. To this end at least one interlocking lug which is capable of being bent outwards elastically or which is extensible is provided which in the attachment position engages an interlocking recess from the rear. With the present design a plug socket 10 in the form of a cap 13 having the shape of a spherical segment is provided, the depth of which is greater than its radius. The corresponding attachment part 4b on the holder 5 or on the handpiece shank 8 is constituted by a spherical head 14 of a shank 4c which is so constructed in size and shape that it is capable of being inserted into the cap 13 with a small clearance or with a clamping force. In order that the edge of the cap 13 is able to move aside in the course of insertion, the base part 2 consists either of elastically extensible material or of elastically flexible material, whereby in the second case the edge of the cap 13 is subdivided by at least one, here three, radial slots 15 into segments 16 which are capable of bending outwards and inwards in radially elastic manner and engage the spherical head 14 from the rear in the inserted position. With the present design the cap is arranged in a circular material extension 17, as a result of which a plug bushing is formed, the wall of which is subdivided into segments 16. The connecting device 4 is consequently constituted by a locking bushing. The cap 13 is preferably so much smaller in size than the spherical head 14 that in the inserted position it exerts a clamping force on the spherical head 14. The clamping force or stiffness is so great that the tool 1 can only be adjusted with a certain pivoting force. The articulation 18 formed in this way is consequently capable of transmitting a minimal torque, guaranteeing a requisite pressure of the working face 12 on the working site. By this means a friction coupling 19 is also formed which slips in the event of a defined transmissible torque being exceeded and consequently limits the transmission of torque and prevents damage to the tooth or to the tool 1 which might be exerted on the tooth for example in the event of a movement of the handpiece and of the tool 1 in the sense of a lever action. The friction coupling 19 consequently also constitutes a safety device.

The articulation 18 has a limited three-dimensional pivoting range of up to about 75°, in particular up to about 60°, in each case from its central position. In an extreme pivoting position according to FIG. 4, in which the tool shank 4c or handpiece shank 8 abuts the material extension, forced oscillations are transmitted to the processing section.

The connecting-device part 4a may be arranged with its centre axis 11 in the longitudinal direction of the processing section 3 or transverse thereto, specifically within the given angular range W of about 90°.

The length of the processing section 3 is somewhat greater than the height of a tooth or the width of a tooth, so that from the side or from the occlusal direction the processing section 3 is able to engage a tooth from the rear. It is advantageous to make the length of the processing section 3 a couple of millimetres longer than the height of the tooth, so that the processing section 3 can be introduced into the tooth pocket (FIG. 6) also in the exterior region of the tooth, in order for example to carry out a periodontosis treatment. The processing section 3 is also suitable for this purpose by reason of its sword or blade shape.

As FIG. 2 shows, with a direction of view towards its broad side the processing section 3 is convergently shaped towards its free end, whereby its useful widths B1 and B2 may amount to about 1.5 to 2.5 mm and 3.5 to 4.5 mm. The thickness d of the blade may amount to about 0.5 to 1 mm. The length L may amount to about 8 to 15 mm, in particular about 8 to 10 mm. With a direction of view towards the narrow side the processing section 3 may extend towards its free end in the shape of a wedge (FIG. 1) or parallel (FIG. 4). In both cases it is advantageous to increase the thickness of the processing section 3 in the transitional region leading to the material extension 17 with a divergently curved working-face section 12v, the curvature of which is adapted, to some extent, to the curvature of a tooth. By this means adjacent face regions of the tooth that is present in the given case can also be processed simultaneously.

As FIG. 3 shows, the front faces of the blade-shaped processing section 3 may be pointed on both sides or on one side, in the latter case preferably on the side facing away from the working face 12.

It is advantageous to arrange on the base part 2 several processing sections 3 which stand apart from one another and/or point in different directions and which, for example, are arranged in the form of a star. With the design according to FIG. 5 three processing sections 3, 3a, 3b are provided which may be of differing construction with respect to their size and/or shape, in particular their length L, L1, L2 and/or thickness.

The tool 1 with its base part 2 and its at least one processing section 3 may consist of elastically flexible steel such as spring steel or rubber or plastic. The working face 2 may be studded in all embodiment examples with aluminium oxide or diamond grains (diamond-faced).

Figure 6:
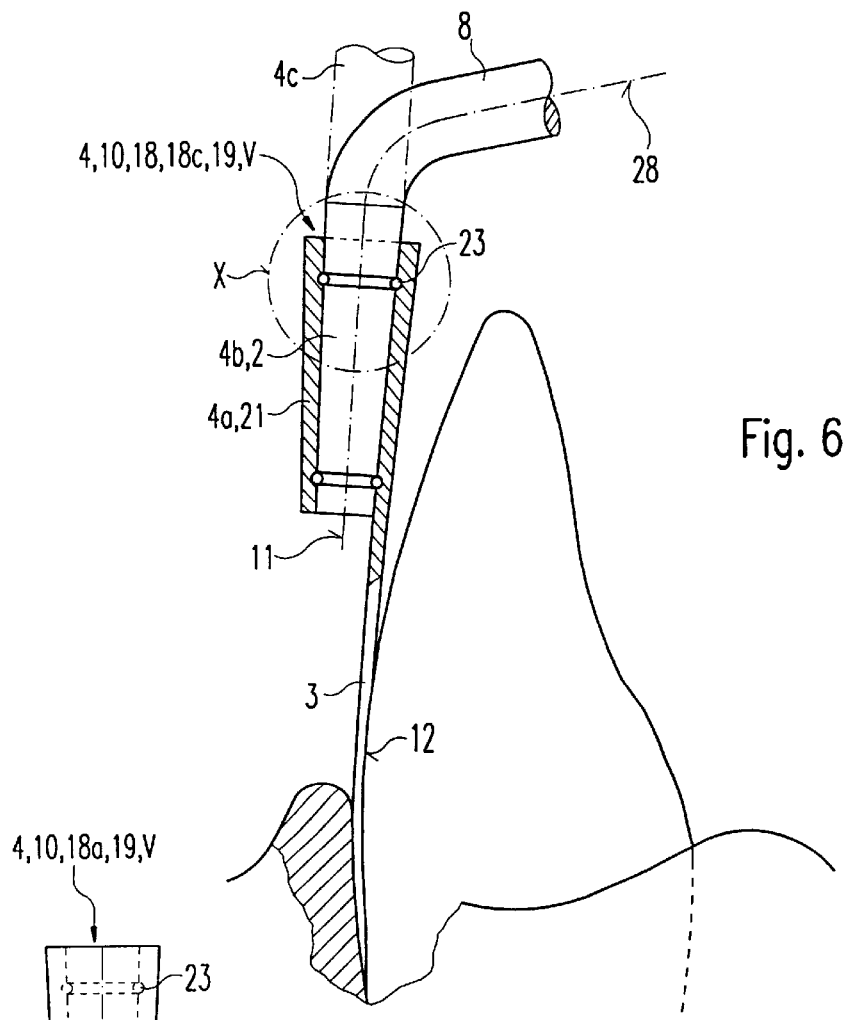
FIG. 6 a tool according to the invention in a modified design in the direction of view transverse to the axis of the tooth.
Figures 7, 8:
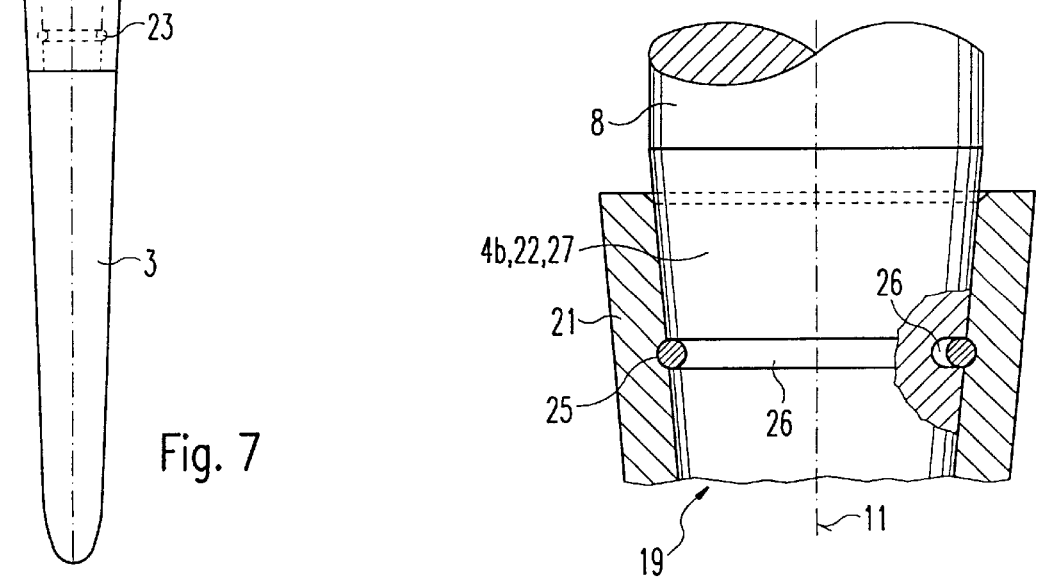
FIG. 7 the tool according to FIG. 6 in the side view from the left.
FIG. 8 the detail X in FIG. 6 on an enlarged scale.

With the design according to FIGS. 6 to 8, in which like or comparable parts are provided with like reference symbols, the base part 2 is constituted by an elongated sleeve 21, which may be closed in the peripheral direction or may be constituted by a C-shaped slotted sleeve, the inner shape of which may be cylindrical or conical, whereby the conical shape is convergent towards the end of the sleeve 21 at which it is connected to the processing section 3 preferably in one piece. The sleeve 21 and the processing section 3 may, for example, be a one-piece bent stamped part. Into the connecting part 4a formed in this way the holder 5 or the shank 4c or the handpiece shank 8 is capable of being inserted with a correspondingly cylindrically or conically shaped tenon 22 forming the connecting part 4b and, in the case of the cylindrical or conical embodiment, is capable of being fixed by means of an interlocking device V and also, in the case of the conical embodiment, by means of clamping force. In this regard there may be a free rotating capacity about the longitudinal axis 11 in the sense of an articulation 18c or by reason of a certain clamping force a fit of the mortise-and-tenon joint in the interlocking position may obtain which is so tight that the torque described previously is guaranteed and in the event of this torque being exceeded the friction coupling 19 which is likewise present comes into operation. In the second case, in which the plug socket 10 is conical, the minimal torque can be adjusted by the cone parts being pushed together more or less tightly, it also being possible for a rigid connection to be created in the case where the parts are tightly pushed together.

The interlocking device V may be realised both in the case of the cylindrical plug socket and in the case of the conical plug socket 10 described previously. As can be gathered from FIG. 8 in particular, the interlocking device V may be constituted by one or two spring elements 23 which are axially spaced from one another and which are constituted, in particular, by spring washers. The spring element 23 is retained either on the sleeve 21 or on the tenon 22, in each instance in a recess, and in the plug-in position is capable of spring deflection into a detent recess that is present on the other part in each case and also capable of being pushed over for the purpose of being detached manually by being pulled out. If the spring element 23 is constituted by a spring washer that is preferably circular in cross-section, both in the inner wall of the sleeve 21 and in the outer wall of the tenon 22 an annular groove 25, 26 is present respectively in which either the spring washer is received with clearance or locks into place in the sense previously described.

The handpiece shank 8, with its connecting end generally designated by 27, may be arranged so as to be straight, at a right angle or oblique with respect to the centre axis 28 of the rod-shaped handpiece 6, in which connection it may preferably include an angle W1 of about 90 to 110°, in particular about 100°, with the centre axis 28. With the design according to FIG. 8 the handpiece shank 8 is bent or angled between its attachment end 27 and its remaining section. This structural design or this shape is advantageous for ergonomic reasons and permits easy-to-handle guidance of the tool 1 with the handpiece 6, in particular in the confined oral cavity of a patient.

If the processing section 3 is abrasive only on one broad side, in the case of a tool 1 that is intended for the approximal tooth region the rear face on the opposite broad side is a smooth face F, as a result of which the adjacent tooth remains unimpaired. Given the existence of an articulation 18a with an axis of articulation directed approximately in the longitudinal direction of the processing section 3, the processing section 3 may be adjusted in each instance by rotation in such a way that the working face 12 is directed rearwards or forwards. By this means it is possible to adapt the processing section 3 to the front or rear side of a tooth and to process these sides. With the design according to FIG. 4, processing sections 3a, 3b following one another in the peripheral direction or located opposite one another may be of inverse construction with respect to their smooth face F, so that one processing section 3a has its working face 12 at the front and the other processing section 3b has its working section 12 to the rear and the smooth face F is present on the opposite side in each case. Since with this design the axis of rotation of the articulation 18b is directed transverse to the longitudinal direction 11 of the processing section 3, here the processing section 3 that is desired in the given case can be pivoted into its working position.

Within the context of the invention it is possible to construct the tool 1 according to FIG. 1 and FIG. 6 (indicated) with a shank 4c pertaining to the tool 1 in two pieces, whereby a connecting device 4d between the tool shank 4c and the handpiece shank 8 is to be provided for retention of the tool 1. With the design according to FIG. 1 such a connecting device 4d is constituted by a seating hole 4e extending lengthwise or transversely within the tool shank 8, into which seating hole tool shank 4c is capable of being inserted and secured by means of an attachment screw 4f which, according to FIG. 1, is screwed frontally into a corresponding threaded hole in the handpiece shank 8 and presses against the tool shank 4c. With this design the connecting device 4d is arranged between the tool 1 and the handpiece shank 8. In contrast, with the design according to FIG. 4 the connecting device 4 is arranged between the tool 1 and the handpiece shank 8. As FIG. 4 likewise shows, this tool shank 8 may be straight or it may be bent out or angled to one side, the end section 27 preferably extending so far beyond the centre axis 28 that the connecting part 4b is radially spaced from the longitudinal axis 28.

The tool 1 according to the invention is suitable for the processing by machining of, in particular, solid body tissue such as bones or teeth pertaining to the human body or to the body of an animal or of substitute material such as is used for prostheses or tooth fillings, for example plastic or metal.

The connecting device 4 or interlocking device V makes it possible for several different tools 1 or processing sections 3 to be mounted or exchanged on the handpiece in easy-to-handle manner and quickly. The processing sections 3 may differ in the sense of fine and coarse, or fine, medium and coarse with respect to their shape and/or size and/or the capacity of their working face 12 to remove material.

The tool or tools 1 or processing sections 3 according to the invention may be employed for the removal of surplus material and for preliminary polishing, in particular after the production of composite fillings and in other respects also in the region close to the gum and below the gum.

What is claimed is:

1. In combination, a medical handpiece and a tool for chip-removing body tissue or a substitute material;

said handpiece comprising a housing having a handpiece shank and an oscillation drive mounted therein, said oscillation drive being connected to said shank to vibrate it at a frequency in the sound or ultrasound range, said shank having a ball head;

said tool being made of an elastic material and having an elongated processing section with an abrasive working surface, and further having a base portion which is integral with said processing section, said base portion having a dome-shaped recess for connecting the tool to the ball head of the handpiece shank, the depth of said recess being larger than the radius of the ball head and forming, together with said ball head, a ball-and-socket joint which transmits vibrations from said handpiece shank to said tool.

2. The handpiece as set forth in claim 1, wherein the ball-and-socket joint is universally moveable to a limited degree.

3. The handpiece as set forth in claim 2, wherein the universal range of movement of said ball-and-socket joint is up to about 75° or up to about 60° with respect to a central position.

4. The handpiece as set forth in claim 1, wherein the ball-and-socket joint is stiff and transmits a torque, whereby the two parts of the ball and socket joint slide relative to one another and form a friction coupling when a defined torque is exceeded.

5. The handpiece as set forth in claim 1, wherein a free edge of the dome-shaped recess is in the form of detent lugs arranged in the region thereof to engage the ball head from the rear.

6. The handpiece as set forth in claim 1, wherein an edge region of the dome-shaped recess is elastically extensible.

7. The tool as set forth in claim 1, wherein the processing section is arranged transversely to the axis of the ball-and-socket joint.

8. The tool as set forth in claim 1, wherein a broad side of the processing section is arranged transversely to the axis of the ball-and-socket joint.

9. The tool as set forth in claim 1, wherein a free end of the processing section is rounded in a convex manner in the direction of view towards a broad side.

10. The tool as set forth in claim 1, wherein the processing section has narrow-sided edges and the narrow-sided edges of the processing section come to a point on one or both sides.

11. The tool as set forth in claim 1, wherein the processing section is curved in the direction of view towards a narrow side or in cross-section.

12. The tool as set forth in claim 1, wherein the processing section comprises broad sides and is abrasive on a broad side that is curved in a concave manner.

13. The tool as set forth in claim 1, wherein the processing section is abrasive on one broad side and has a smooth face on another broad side.

14. The handpiece as set forth in claim 1, wherein the tool comprises a plurality of processing sections which are provided in a distributed manner about the ball-and-socket joint.

15. The tool as set forth in claim 14, wherein the processing sections are of different configurations.

16. The tool as set forth in claim 14, wherein the processing sections are abrasive on different sides and have a smooth face.

17. The tool as set forth in claim 14, wherein the processing sections have different thicknesses and/or lengths.

18. The handpiece as set forth in claim 1, wherein an edge region of the dome-shaped recess is subdivided into segments which can be bent outwards elastically.

19. The tool as set forth in claim 1, wherein a processing section is abrasive on the broad side thereof that is curved in a concave manner.

* * * * *